(12) United States Patent
Haemmerich et al.

(10) Patent No.: US 11,511,028 B2
(45) Date of Patent: Nov. 29, 2022

(54) EXTRACORPOREAL DRUG REMOVAL FOR INTRAVASCULAR TRIGGERED DRUG DELIVERY SYSTEMS

(71) Applicant: MUSC Foundation for Research Development, Charleston, SC (US)

(72) Inventors: Dieter Haemmerich, Charleston, SC (US); Anjan Motamarry, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 877 days.

(21) Appl. No.: 16/404,726

(22) Filed: May 6, 2019

(65) Prior Publication Data
US 2019/0336671 A1    Nov. 7, 2019

Related U.S. Application Data

(60) Provisional application No. 62/666,883, filed on May 4, 2018.

(51) Int. Cl.
| | |
|---|---|
| *A61M 1/34* | (2006.01) |
| *A61K 41/00* | (2020.01) |
| *A61M 1/36* | (2006.01) |
| *A61K 49/00* | (2006.01) |

(52) U.S. Cl.
CPC ....... *A61M 1/3486* (2014.02); *A61K 41/0028* (2013.01); *A61M 1/369* (2013.01); *A61M 1/3615* (2014.02); *A61M 1/3621* (2013.01); *A61M 1/3681* (2013.01); *A61K 49/0084* (2013.01); *A61M 1/342* (2013.01); *A61M 1/3679* (2013.01); *A61M 2205/3306* (2013.01)

(58) Field of Classification Search
CPC ........ A61M 1/34; A61M 1/36; A61M 1/3681; A61M 2205/3306; A61M 1/369; A61M 1/3621; A61M 1/3486; A61M 1/3615; A61M 1/342; A61M 1/3679; A61K 41/0028
See application file for complete search history.

(56) References Cited

U.S. PATENT DOCUMENTS

| | | | |
|---|---|---|---|
| 9,541,544 B1 * | 1/2017 | Hobbs | A61M 1/3615 |
| 2009/0048552 A1 * | 2/2009 | Hassan | A61M 1/84 604/500 |
| 2013/0343953 A1 * | 12/2013 | Kline | A61M 1/3618 210/806 |
| 2017/0246375 A1 * | 8/2017 | Spearman | A61M 1/1629 |

* cited by examiner

*Primary Examiner* — Leslie R Deak
(74) *Attorney, Agent, or Firm* — Riverside Law LLP

(57) ABSTRACT

A system for reducing toxicity from intravascular triggered drug delivery includes a chamber comprising an inflow port, an outflow port, and a filter positioned upstream of the outflow port. A trigger module is configured to trigger the release of a drug from an intravascular triggered drug delivery system present in blood in the chamber. A method for reducing toxicity from intravascular triggered drug delivery includes the steps of removing blood comprising an intravascular triggered drug delivery system from a patient's vascular system and delivering the blood to a chamber, applying a trigger to the blood to release a drug from the intravascular triggered drug delivery system, filtering the drug from the blood, and returning the filtered blood to the patient.

7 Claims, 15 Drawing Sheets

EXTRACORPOREAL DRUG REMOVAL FOR INTRAVASCULAR TRIGGERED DRUG DELIVERY SYSTEMS

CROSS-REFERENCE TO RELATED APPLICATIONS

This application claims priority to U.S. provisional application No. 62/666,883 filed on May 4, 2018 incorporated herein by reference in its entirety.

BACKGROUND OF THE INVENTION

Toxicity is a limiting factor of all current chemotherapy approaches. Current chemotherapies are limited by (1) insufficient delivery of drug to targeted tumors, often resulting in tumor recurrence, and (2) toxicity to other tissues and organs that limit amount of chemotherapy that can be administered. Numerous nanoparticle drug delivery systems have been investigated with the goal of delivering more drug to the tumor. An alternate method of improving treatment efficacy that has been scarcely investigated is elimination of drug not delivered to the tumor.

Nanoparticles are one particular drug delivery systems (DDS) where release of the drug associated within the DDS (e.g. chemotherapy encapsulated within a liposomal carrier) occurs within the vasculature of the target region (e.g. tumor). This type of DDS will be referred to herein as "intravascular triggered DDS" (IVDDS). Recent studies suggest that IVDDS are highly effective in delivering drugs at high concentration to a localized, targeted tissue region [1, 2].

Generally, IVDDS are administered systemically (e.g. intravenous infusion) and circulate within the systemic blood circulation. Depending on the type of IVDDS, release of the drug is triggered within the target region by the appropriate trigger signal (e.g. via localized heating for temperature sensitive liposomes (TSL), or ultrasound for microbubble based IVDDS). Dependent on IVDDS, the trigger signal can be applied externally or internally (heat, ultrasound, laser, microwave, light, etc.), or can be a biological signal specific to the targeted tissue (e.g. pH). Following the localized drug release within the vasculature, drug is extracted by targeted tissue and taken up by cells within the target region. Unique to IVDDS, drug uptake by cells is limited to the duration when the trigger for release is applied, e.g. 30-60 minutes in prior studies [1, 2]. For comparison, other DDS typically require many hours or days to accumulate in the target region, and release the drug at similar slow rates.

Toxicity results from uptake of DDS and/or drug in non-targeted tissue regions. In one type of conventional treatment, traditional liposomes (which are not IVDDS) are eliminated from the patient's systemic circulation by filtration plasmapheresis, considerably reducing toxicity in human patients [3]. While the same approach may be applied also to some IVDDS, this method is not highly effective (2-3 h to eliminate 60-70% of circulating liposomes [3]). In fact, since the plasma half-life of some IVDDS such as temperature sensitive liposomes (TSL) is only 1-2 hours, such an approach may not be applicable or effective for such IVDDS.

Thus, there is a need in the art to remove any drug still present in systemic circulation from the body after triggered release and uptake by cells in the target region has occurred, thus avoiding any toxicity from IVDDS that did not completely release their content without affecting efficacy.

SUMMARY OF THE INVENTION

In one embodiment, a system for reducing toxicity from intravascular triggered drug delivery includes a chamber comprising an inflow port, an outflow port, and a filter positioned upstream of the outflow port, and a trigger module configured to trigger the release of a drug from an intravascular triggered drug delivery system present in blood in the chamber. In one embodiment, the trigger module comprises a heat source. In one embodiment, the trigger module comprises a ultrasound source. In one embodiment, the trigger module comprises a laser source. In one embodiment, the trigger module comprises a light source. In one embodiment, the trigger comprises a biological signal. In one embodiment, the system includes a first fluorescence light source and sensor disposed upstream of the inflow port and a second fluorescence light source and sensor disposed downstream of the outflow port. In one embodiment, the filter is a carbon haemoperfusion filter. In one embodiment, the filter is a charcoal filter. In one embodiment, the system includes a first light source configured at a specified wavelength or spectrum to excite fluorescence or cause spectral light absorption of a specific drug, a first sensor configured to measure fluorescence or absorption at a wavelength or spectrum for a specific drug, wherein the first light source and first sensor are located in proximity of the blood before blood filtration, and where sensor is located such that fluorescence or absorption caused by the light source can be detected, a second light source and sensor equivalent to first source and sensor, in proximity of the blood, located after blood filtration, a controller configured to determine drug concentration in blood before and after filtration based on sensor measurements before and after filtration, and calculate dose of drug removed based on concentration measurements before, and after filtration and known blood flow rate, and a display to indicate the amount of drug removed in real-time to the operator of the system.

In one embodiment, a method for reducing toxicity from intravascular triggered drug delivery includes the steps of removing blood comprising an intravascular triggered drug delivery system from a patient's vascular system and delivering the blood to a chamber, applying a trigger to the blood to release a drug from the intravascular triggered drug delivery system, filtering the drug from the blood, and returning the filtered blood to the patient. In one embodiment, the trigger comprises the application of heat. In one embodiment, the trigger comprises the application of ultrasound. In one embodiment, the trigger comprises the application of a laser. In one embodiment, the trigger comprises the application of light. In one embodiment, the trigger comprises the application of a biological signal. In one embodiment, the method includes the step of plasma filtration, fluorescence or light absorption sensing performed on plasma.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1:
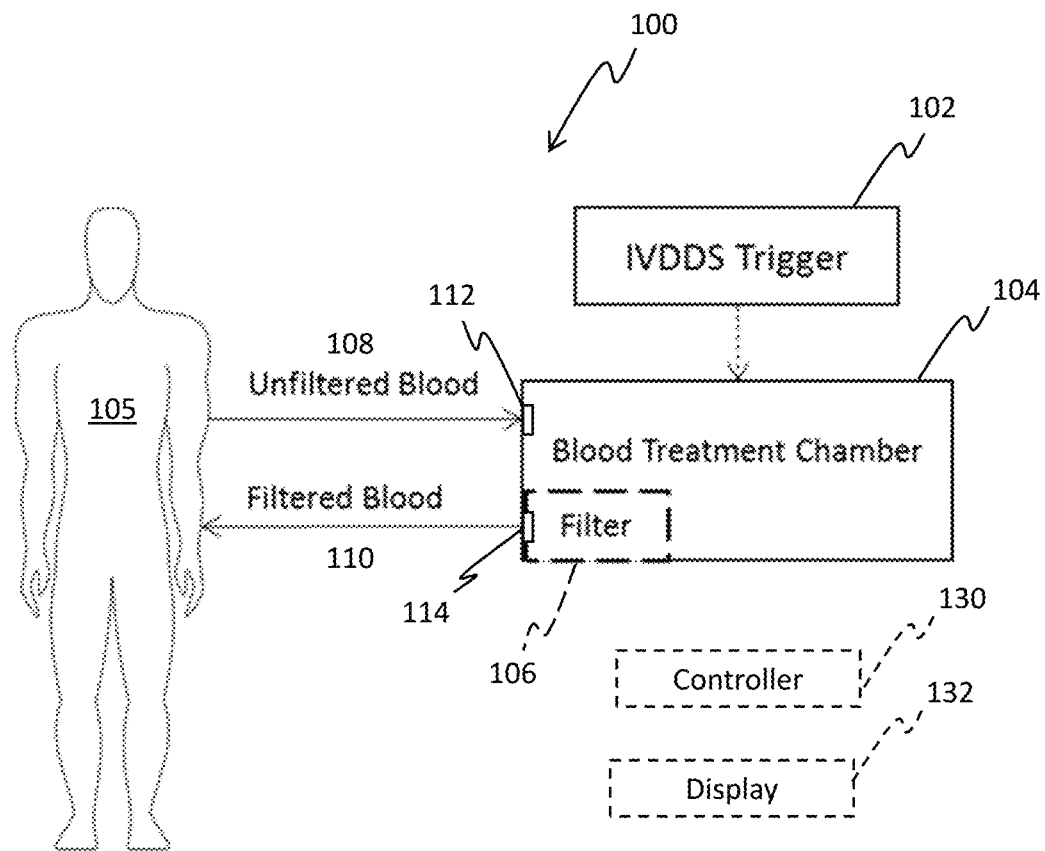
FIG. 1 is a diagram of a system for reducing toxicity from intravascular triggered drug delivery according to one embodiment.

It is to be understood that the figures and descriptions of the present invention have been simplified to illustrate elements that are relevant for a more clear comprehension of the present invention, while eliminating, for the purpose of clarity, many other elements found in systems and methods of reducing toxicity from intravascular triggered drug delivery. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein are systems and methods for reducing toxicity from intravascular triggered drug delivery.

The system and method described herein removes any drug still present in systemic circulation from the body after triggered release and uptake by cells in the target region has occurred, thus avoiding any toxicity from IVDDS that did not completely release their content (which includes the majority of administered drug) [2], without affecting efficacy. Since with this approach IVDDS are present within the systemic circulation only for a limited duration, toxicity is greatly reduced. The method works considerably faster (minutes to one hour) compared to conventional methods with superior efficacy. IVDDS can include a variety of drug delivery systems such as liposomes, microbubbles, polymeric nanoparticles, micelles, among others. Any DDS that can be administered into blood circulation and releases drug in response to a trigger may qualify as IVDDS.

Embodiments of the system and method described herein apply among other IVDDS to a new type of thermally sensitive liposomes (TSL) that release the contained drug within the vasculature of the targeted tumor region. These TSL rapidly (~sec) release the contained drug when heated to fever range temperatures (>40° C.). The goal is to locally heat the tissue region where a known tumor is present or suspected, to cause local chemotherapy release from TSL in the target region while limiting drug uptake in other tissues. TSL are highly effective in delivering drugs at high concentration to a localized, targeted tissue region. In preclinical studies, tumor drug concentrations up to 30× higher compared to administration of unencapsulated drug can be achieved. A number of technologies are clinically available for localized tissue heating to defined target temperatures, such as laser, microwave, or focused ultrasound.

Toxicity results from uptake of liposomes and/or unencapsulated drug in non-targeted tissue regions (e.g. heart). Since with TSL, drug delivery to the targeted region occurs only during the duration of localized hyperthermia (~30-60 min), any remaining liposomal drug after heating does not contribute therapeutically and only results in toxicity. Embodiments of the system and method described herein removes any drug still present in systemic circulation from the body after hyperthermia mediated delivery, thus preventing any toxicity from TSL that did not completely release their content. Due to the small tumor volume compared to systemic tissue volume, only a fraction of administered TSL release the drug in the target region during hyperthermia. Over 80% of the administered drug dose is still encapsulated after hyperthermia and contributes towards toxicity.

Generally, treatments utilizing embodiments of the system and method described herein includes the steps of (1) Administration of IVDDS, (2) Triggered release of drug from IVDDS within targeted tissue region, and (3) Extracorporeal removal of drug from systemic circulation via the device and method (explained in further detail below).

Step (3) employs an extracorporeal blood circuit, e.g. such as is used in dialysis patients. An extracorporeal device employing the filtration method is connected to the systemic circulation of a patient, e.g. via needle or catheter. The blood of a patient flows through the device, drug still present in the blood is removed, and the filtered blood is returned to the patient. Potentially, a single double-lumen catheter inserted into a vessel can be employed for this approach for both access and return of blood.

With reference now to FIG. 1, a system and method 100 for reducing toxicity from intravascular triggered drug delivery is shown in the blood circuit diagram according to one embodiment. Unfiltered blood 108 is drawn from the patient and directed to a blood treatment chamber 104 having an inflow port 112 and an outflow port 114. Depending on the IVDDS, the required release trigger 102 is applied to the blood external to the body 105 within the treatment chamber 104 (e.g. blood is heated to facilitate drug release from TSL; or e.g. ultrasound is applied to blood to release drug from microbubbles). Following drug release from IVDDS (ideally is complete release) within the treatment chamber 104, the released drug is extracted from the blood with adequate filters 106 (e.g. carbon haemoperfusion filters in the case of the chemotherapeutical drug Doxorubicin [4]) located upstream of the outflow port 114. A controller 130 can be used to communicate and sync functionality of system components, and for monitoring filtering progress and sensor feedback, sending feedback or instructions to a display 132, and providing input parameters to the system. Several filter types and filtration methods are available for human patients for hemofiltration or plasma filtration that can be adapted for the proposed method. Such filtration is highly effective, and removes 80-90% of drug within a single pass (i.e. can remove most drug from the patients circulation within several minutes to an hour, depending on blood flow through the external device). The filtered blood 110 is returned to the patient 105. Note that IVDDS are still present, but the drug that was contained or associated with IVDDS has been removed. Thus the approach is dissimilar to actual removal of IVDDS from the circulation as described in relation to conventional systems and methods.

Figure 2:
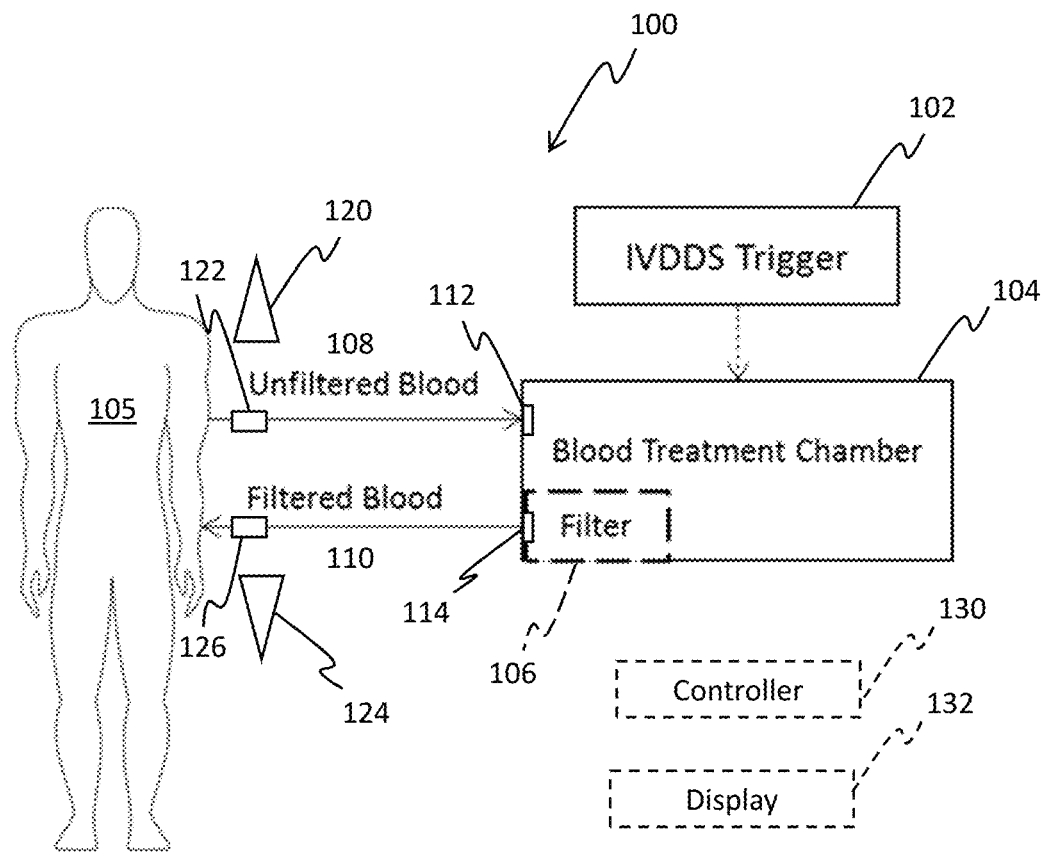
FIG. 2 is a diagram of a system for reducing toxicity from intravascular triggered drug delivery according to one embodiment.

Knowledge of the amount of drug removed can be beneficial since doctors estimate potential side effects depending on drug dose that is administered to the patient. Further, for certain drugs such as chemotherapies there is a maximum dose that can be administered to the patient, and any removed drug would not contribute towards administered dose. In one embodiment, fluorescence measurement (for fluorescent drugs such as doxorubicin, idarubicin, daunarubicin, epirubicin, valrubicin, methathrexate) is used in a method to determine the amount of drug removed. In one embodiment, other compounds can be measured by light absorption spectra. With reference now to FIG. 2, in one embodiment, a system for determining amount of drug removed during filtration with the system can include a first light source 120 at a specified wavelength or spectrum to excite fluorescence or cause spectral light absorption of a specific drug, and a first sensor 122 that measures fluorescence or absorption at a wavelength or spectrum for a specific drug. The first light source 120 and sensor 122 are located in proximity of the unfiltered blood (e.g. adjacent to tubing) before blood filtration, and the sensor is located such that fluorescence or absorption caused by the light source can be detected (e.g. sensor and source are located on opposite sides of a translucent tube, or adjacent on same side of the tube). A second light source 124 and sensor 126 equivalent to the first light source 120 and sensor 122, are in proximity of the blood (e.g. adjacent to tubing), located after blood filtration. An algorithm (e.g. based on look-up table or calibration curve) determines drug concentration in blood before and after filtration based on sensor measurements before and after filtration. An algorithm calculates the dose of drug removed based on concentration measurements before, and after filtration and known blood flow rate. A method to display the amount of drug removed in real-time to the operator of the system (e.g. medical staff) is included. Plasma filtration can be used in the system and method, and fluorescence or light absorption sensing is performed on plasma.

Figure 3:
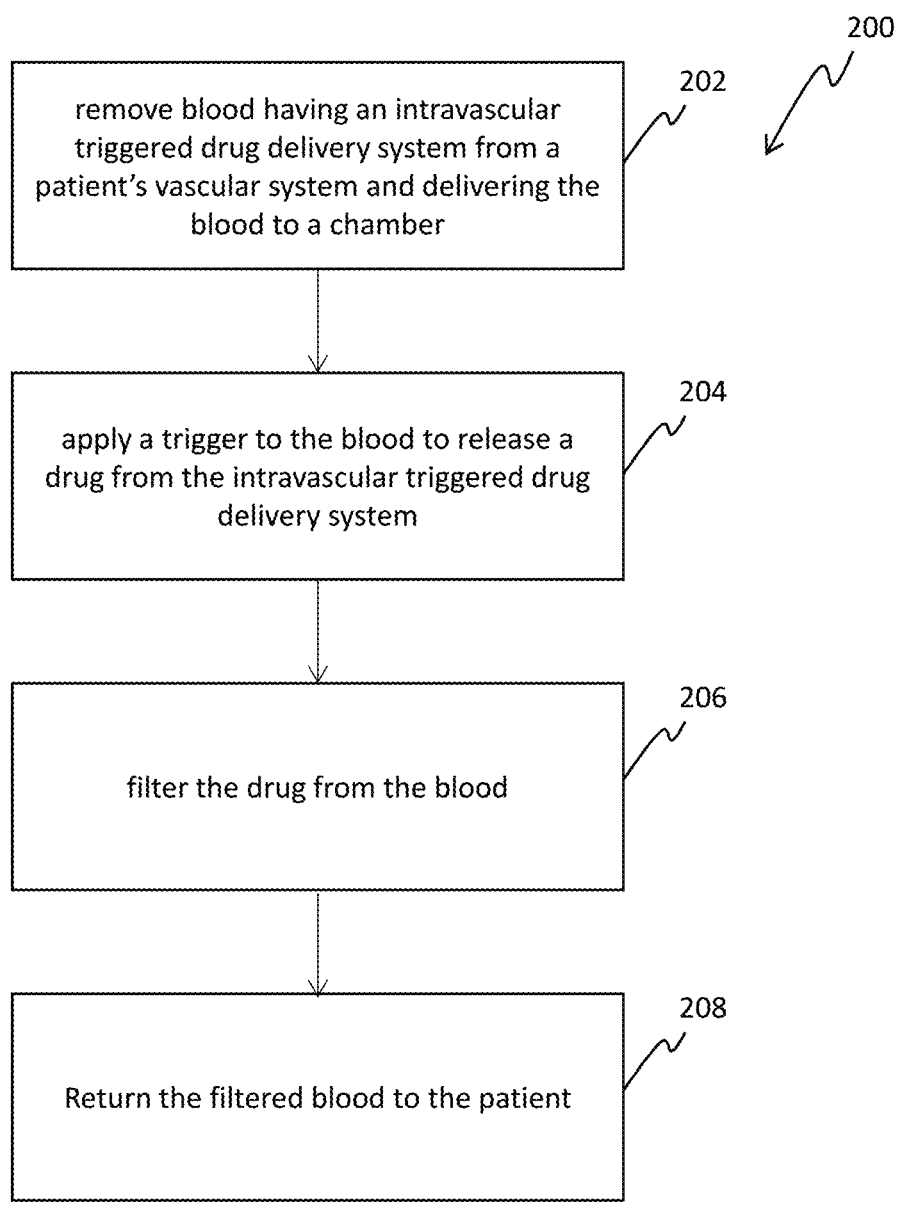
FIG. 3 is a flow chart of a method for reducing toxicity from intravascular triggered drug delivery according to one embodiment.

A method 200 for reducing toxicity from intravascular triggered drug delivery is described with reference to FIG. 3 according to one embodiment. The method 200 includes the steps of removing blood comprising an intravascular triggered drug delivery system from a patient's vascular system and delivering the blood to a chamber 202, applying a trigger to the blood to release a drug from the intravascular triggered drug delivery system 204, filtering the drug from the blood 206, and returning the filtered blood to the patient 208.

A method 300 for determining an amount of drug removed during filtration is described with reference to FIG. 4 according to one embodiment. The method 300 includes the steps of determining or measuring the amount of encapsulated drug 302, determining or measuring the remaining drug after filtration 304, and determining or measuring the amount of drug removed 306. In one embodiment, a first sensor is located at tubing before filtration and senses drug fluorescence, which is converted to drug concentration based on a calibration curve. In one embodiment, a second sensor located in tubing after filtration senses drug fluorescence, which is converted to drug concentration. Alternatively, the method can be applied to plasma (if plasma filtration is used), which is more accurate since plasma is translucent, simplifying measurements. Based on flow rate and difference between these two measurement, the amount of drug removed during filtration is calculated. This amount is presented to the treating medical staff (physician, nurse, etc.) via a real-time display. Based on the display, the medical staff can decide when filtration should be stopped, i.e. when most of drug has been removed.

Embodiments of the system and method described herein can provide improved outcomes for patients and healthcare facilities. Pharmaceutical companies, particularly those working on this class of drug delivery systems would also benefit. Examples of this class of drug delivery systems includes temperature sensitive liposomes, other temperature sensitive carriers (e.g. polymers), and microbubble based drug delivery systems, and various triggered nanoparticles that are responsive to light, electric fields, magnetic fields, pH, and enzymes [5].

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Experimental Example 1

Figure 5A:
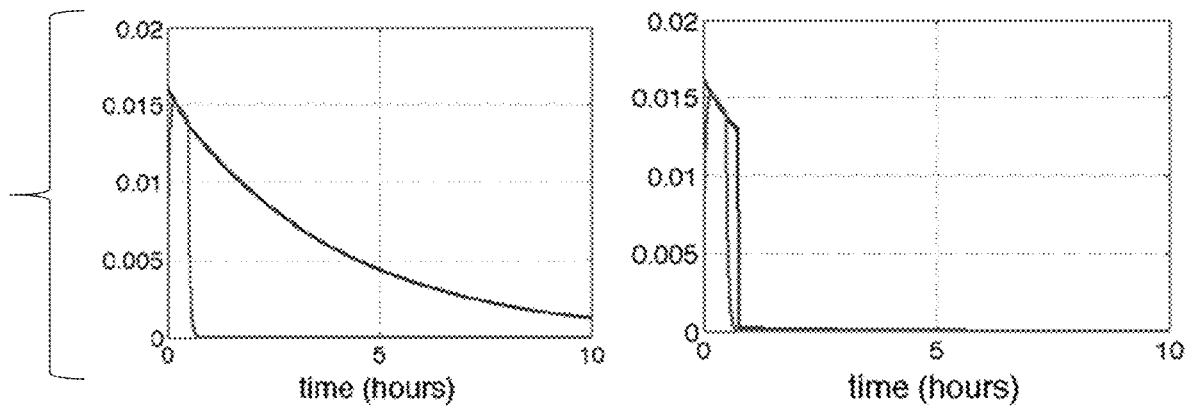
FIG. 5A shows plasma concentration of drug encapsulated within IVDDS (top curve), and released drug within target region (bottom curve), assuming release trigger is present for 0.5 hours according to one embodiment. Left: without filtering; right: with filtering, where at t=0.75 min, remaining encapsulated drug is removed from systemic plasma. Note that this does not impact amount of drug delivered to target region.
Figure 5B:
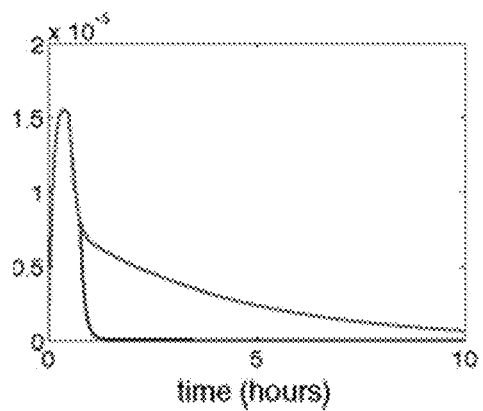
FIG. 5B shows systemic plasma concentration of bioavailable drug (i.e. after release), without (top curve) and with filtering (bottom curve) according to one embodiment. Plasma AUC is commonly used as predictor of systemic toxicity, and is reduced by a factor of ~3.
Figure 5C:
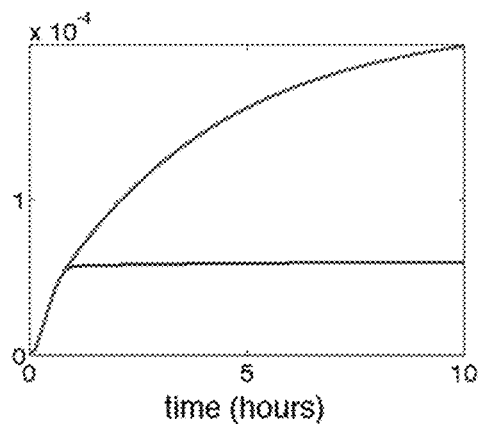
FIG. 5C shows drug concentration taken up by systemic lump tissue compartment (representing all bodily tissues) without (top curve) and with filtering (bottom curve) according to one embodiment. Systemic tissue concentration is reduced by factor of ~3 as well.

Computational modeling data demonstrates the potential benefit of the system and method described herein, reducing drug uptake in non-targeted tissue regions to a small fraction (~10-40%, depending on properties of IVDDS and drug), without affecting drug delivery to the targeted region. The following graphs are adapted from a computer model [2], adapted to simulate the filtering method. With reference to FIG. 5A, plasma concentration of drug encapsulated within IVDDS (blue), and released drug within target region (green), assuming release trigger is present for 0.5 hours is shown. Left: without filtering; right: with filtering, where at t=0.75 min, remaining encapsulated drug is removed from systemic plasma. Note that this does not impact amount of drug delivered to target region. With reference now to FIG. 5B, systemic plasma concentration of bioavailable drug (i.e. after release), without (green) and with filtering (blue) is shown. Plasma AUC is commonly used as predictor of systemic toxicity, and is reduced by a factor of ~3. With reference now to FIG. 5C, drug concentration taken up by systemic lump tissue compartment (representing all bodily tissues) without (green) and with filtering (blue) is shown. Systemic tissue concentration is reduced by factor of ~3 as well. FIGS. 5A-5C suggest considerable reduction in toxicity without affecting efficacy of drug delivery to the target tissue when the method is employed.

Experimental Example 2

In Vivo Experimental Data

Figure 6A:
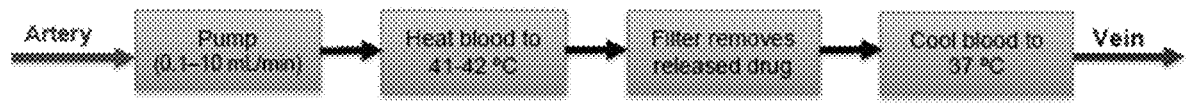
FIG. 6A is a diagram of a prototype blood circuit and FIG. 6B is a diagram of TSL release over time according to one embodiment.
Figure 6B:
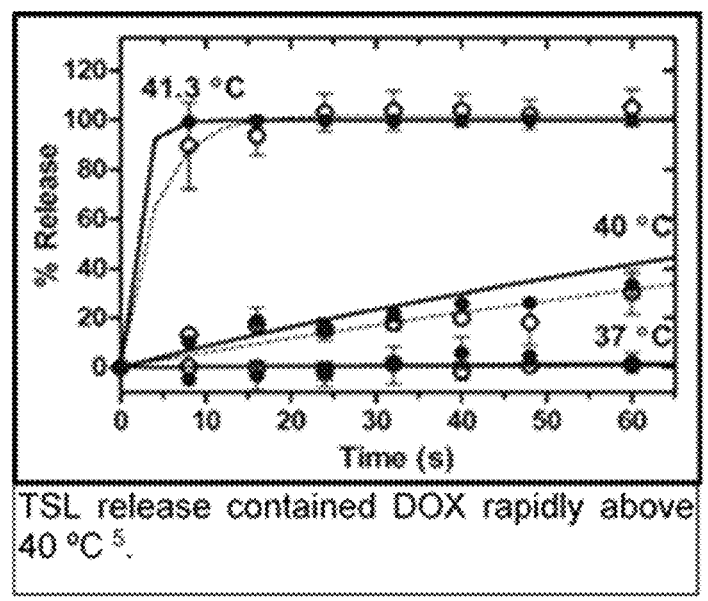
Figure 7:
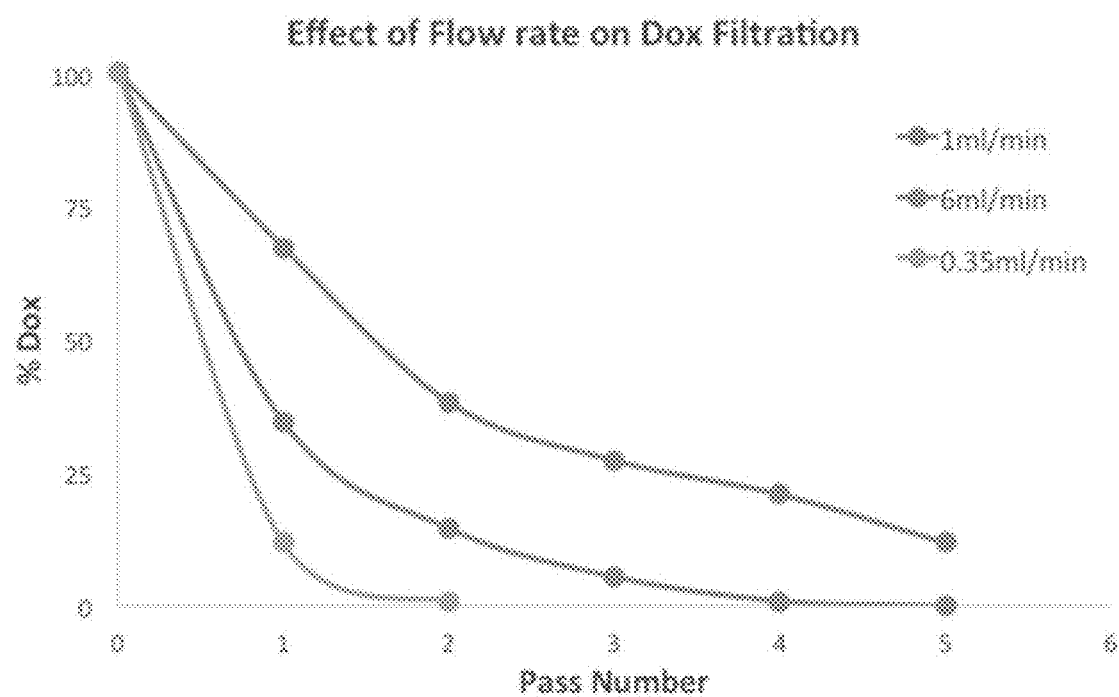
FIG. 7 is a graph of the effect of flow rate on Dox filtration. Filter efficacy was tested with PBS under varying flow rates (0.35-6 ml/min), and for 0-5 passes. A solution containing 200 ug/ml was pumped through the filter, and amount of drug remaining at the filter outlet was measured.

With reference now to FIGS. 6A and 6B, a prototype device was built including a pump, a custom-designed heat exchanger, and a filtration element based on activated charcoal. The extracorporeal device filters blood accessed via an arterial catheter. Blood is pumped through a heat exchanger that heats blood to 41-42° C. to release Dox from TSL. Subsequently a filter removes released, unencapsulated Dox, and a second heat exchanger cools blood to body temperature before returning the filtered blood to venous circulation. With reference now to FIG. 7, the device was tested in vitro with plasma and blood to confirm adequate performance under physiologically relevant flow rates.

In vitro tests: Filter efficacy was tested with PBS under varying flow rates (0.35-6 ml/min), and for 0-5 passes. A solution containing 200 ug/ml was pumped through the filter, and amount of drug remaining at the filter outlet was measured.

A rat model was developed where the carotid artery and jugular vein were catheterized. In anesthetized and shaved animals, a 0.5 cm midline skin incision was made between the scapulae using a surgical scissor. The rat was then repositioned in the dorsal position. Legs were gently restrained to each side of the table using or tape while maintaining anesthesia. Two rolled sterile 4×4 gauze was placed under neck to slightly hyperextend for better exposure. A 2 cm ventral cervical skin incision right of the midline of the neck at the level of the clavicle was made using a scalpel.

Using a hemostat and blunt dissecting, the omohyoid muscle was cut longitudinally to expose the carotid artery and isolate a 5 mm section of the vessel. The vagus nerve was completely separated from the artery. Using a monofilament nylon or silk thread, a loose tie was placed on the caudal end of the vessel, with another tie the cranial end of the vessel was tied off and a bulldog clamp caudally is placed above the thread to stop the blood flow following the incision. With a micro surgical scissor, an incision large enough to pass the catheter was made. The arterial catheter was inserted towards the heart with the assistance of the micro dissecting hook or vessel pick and forceps. A smooth needle holder without lock was used to hold the catheter inside the vessel and the bulldog clamp was then removed. The catheter was advanced with a pair of forceps until the anchor touches the vessel. The loose caudal ligature was then tied around the catheter and vessel to secure, but not so tight as to occlude, the catheter.

Similar to the carotid artery catheterization, the jugular vein was also catheterized by visualizing and isolating the vein. Using a straight hemostat and blunt dissection, a tunnel of 5 cm was tunneled subcutaneously behind the ear and through the incision between the scapulae. The catheters were passed through the tube and the tube then removed. The ventral incision was closed with stainless steel wound clips, and the dorsal incision with a monofilament sutures to secure the exteriorized catheters in place. Catheters were filled with heparinized saline. The externalized catheters were placed into a sterile protective plastic sheath designed and made in the lab. After the catheters have been implanted into the jugular vein and Carotid artery, the incision was closed by discontinuous 4-0 absorbable sutures.

Temperature sensitive liposomes filled with doxorubicin were administered to the animal, and then extracorporeal filtration was initiated with the prototype circuit. Blood samples were obtained at regular intervals to confirm ability to remove the chemotherapy from systemic circulation (see FIGS. 8 and 9). Blood from the catheterized artery was passed through the filter and then was reintroduced back to the animal through the catheterized vein.

Figure 8:
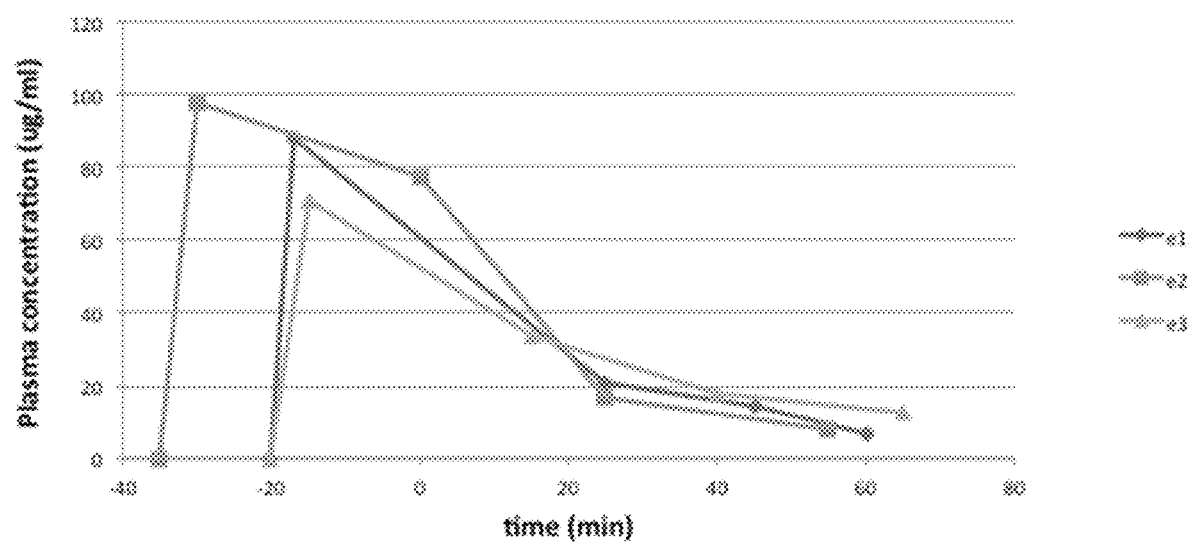
FIG. 8 is a graph of plasma concentration levels over time according to one embodiment. Plasma concentration of filtration experiment in 3 animals is shown. Filtration was initiated at t=0 min. The system was able to consistently remove 30% within ~60 minutes.

ECC filtration in vivo: With reference to FIG. 8, results of plasma concentration of filtration experiment in 3 animals is shown. Filtration was initiated at t=0 min. The system was able to consistently remove 30% within ~60 minutes. These results demonstrate that the method can effectively remove chemotherapy from systemic circulation as intended.

Figure 9:
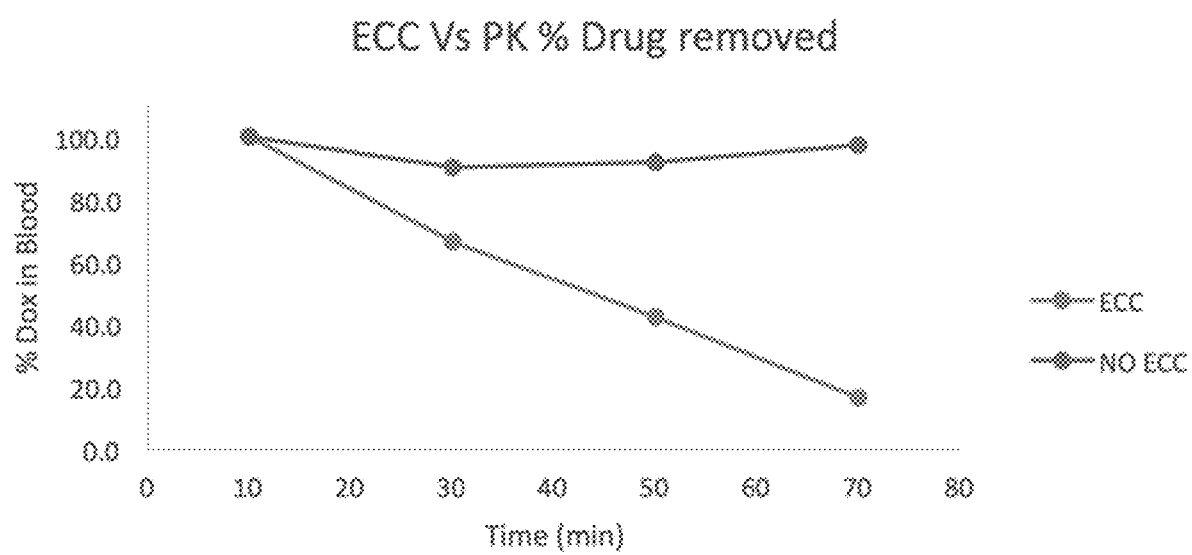
FIG. 9 is a graph of a comparison of plasma PK of an animal without filtration (top curve), with an animal where extracorporeal filtration was performed (bottom curve) according to one embodiment.

In vivo results: With reference to FIG. 9, results of a comparison of plasma PK of an animal without filtration (top curve), with an animal where extracorporeal filtration was performed (bottom curve) are shown. This outcome demonstrates a significant advantage facilitated by embodiments of the system and method described here.

Experimental Example 3

Pharmacokinetic Model

A simple two-compartment pharmacokinetic model was created to simulate removal of encapsulated (liposomal) doxorubicin from systemic circulation in both rat and human. The model included a systemic plasma compartment, as well as a compartment simulating the filter.

Figure 10A:
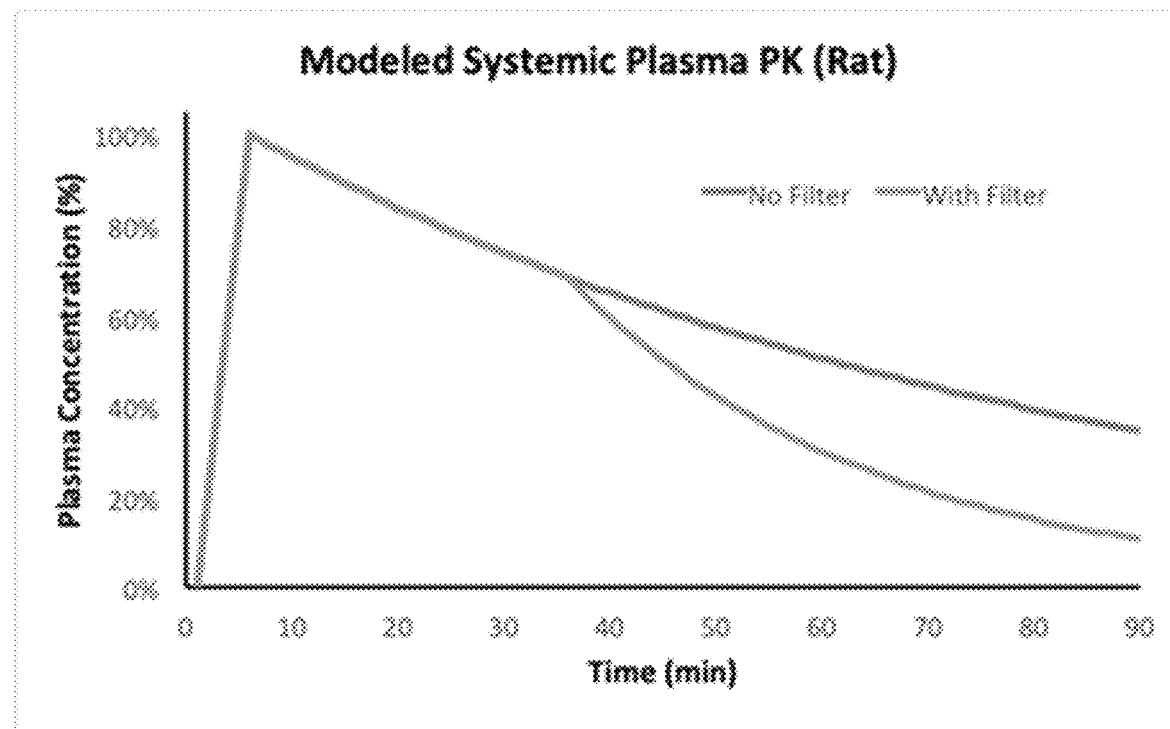
FIG. 10A is a graph of plasma concentration of encapsulated drug in a pharmacokinetic (PK) model.
Figure 10B:
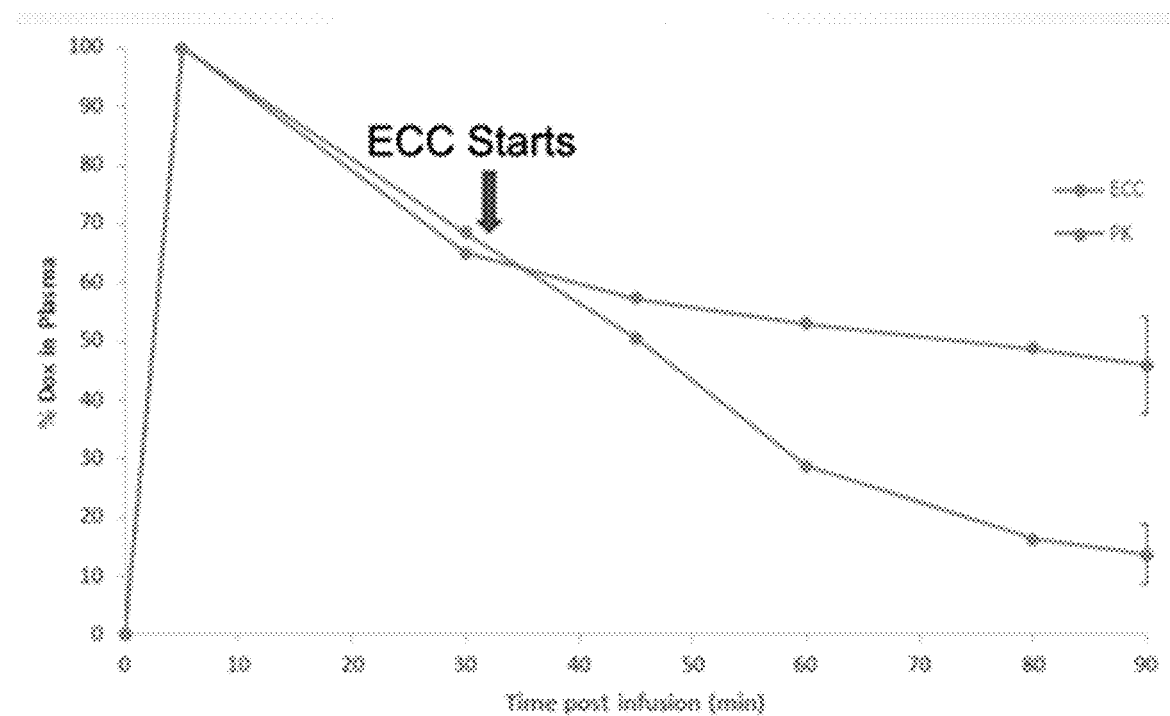
FIG. 10B is a graph from in vivo studies (n=3 rats per group) according to one embodiment. Encapsulated drug (thermosensitive liposomal doxorubicin (TSL-Dox)) was injected during the first 5 min, and filtration was started 30 min after injection (indicated by red arrow in (FIG. 10B)), assuming that heat-activated delivery takes place during this 30 min.

Rat PK Model:

Clearance of encapsulated drug was modeled based on in vivo rat studies (FIG. 1B). Physiologic parameters (blood volume, plasma volume, etc.) were estimated based on animal weight. We assumed blood flow through the filter at the rate used in vivo (350 uL/min), and considered the administered dose used in vivo (1.75 mg). We assumed injection of encapsulated drug during the first 5 min, and started filtration 30 min after drug injection (same conditions as in in vivo studies). Output of the model included plasma concentration of encapsulated drug, as well as amount of drug removed considering varying filter efficacies. FIG. 10A shows the plasma concentration of encapsulated drug without filter, and with filtering. For comparison, in vivo results are shown in FIG. 10B.

Plasma concentration of encapsulated drug (FIG. 10A) in a pharmacokinetic (PK) model, and (FIG. 10B) from in vivo studies (n=3 rats per group). Encapsulated drug (thermosensitive liposomal doxorubicin (TSL-Dox)) was injected during the first 5 min, and filtration was started 30 min after injection (indicated by the arrow in (FIG. 10B)), assuming that heat-activated delivery takes place during this 30 min.

Figure 11:
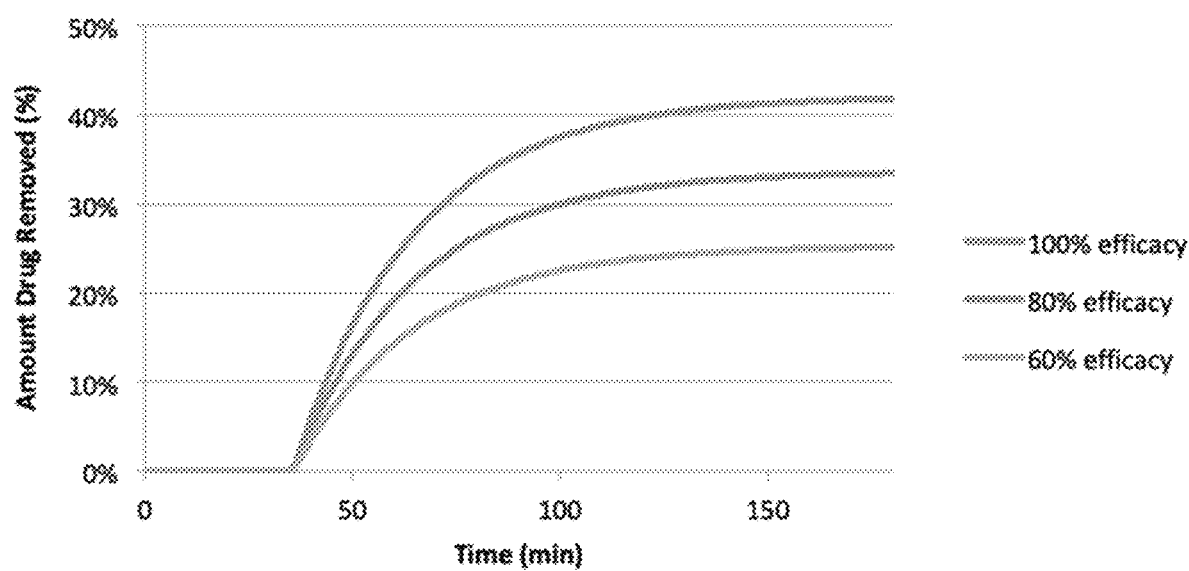
FIG. 11 is a graph of the total amount of drug removed (% of administered dose) for different filter efficacies according to one embodiment. In in vivo studies, filter efficacy was 80% initially and dropped to ~50% at 40 min after start of filtration. Total drug amount removed in vivo was ~30% of the injected dose, which is in the range predicted by the PK models for this range of filter efficacies.

With reference now to FIG. 11, the total amount of drug removed (% of administered dose) for different filter efficacies is shown. In our in vivo studies, filter efficacy was 80% initially and dropped to ~50% at 40 min after start of filtration. Total drug amount removed in vivo was ~30% of the injected dose, which is in the range predicted by the PK models for this range of filter efficacies.

Figure 12:
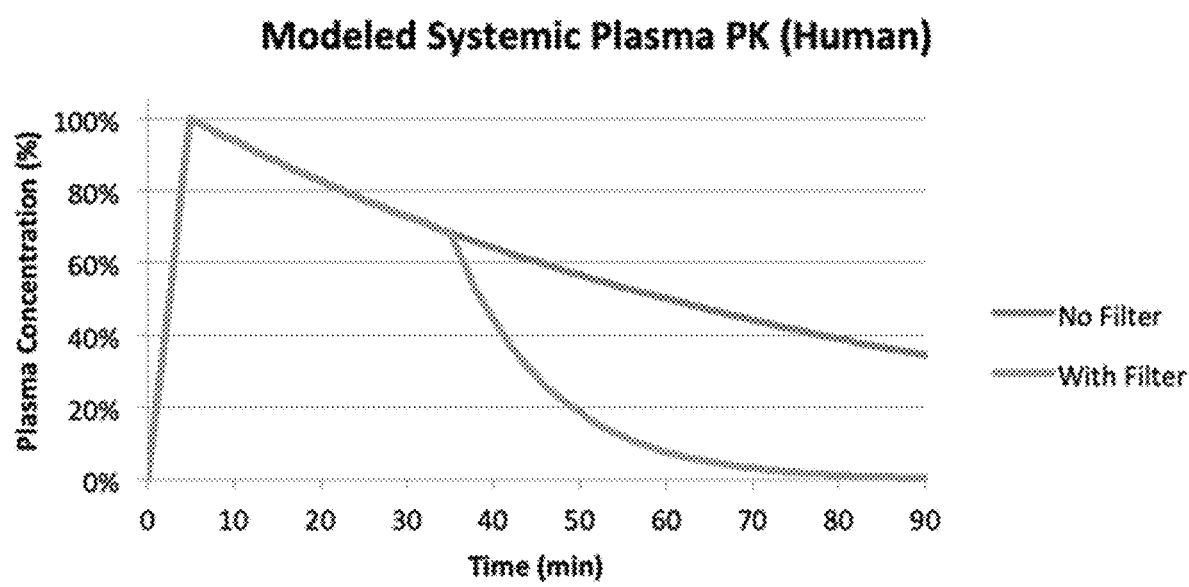
FIG. 12 is a graph of plasma concentration of encapsulated drug in pharmacokinetic (PK) model based on the TSL-Dox formulation currently in human trials according to one embodiment. Encapsulated drug (thermosensitive liposomal doxorubicin (TSL-Dox)) was administered during the first 5 min, and filtration was started 30 min after drug administration.
Figure 13:
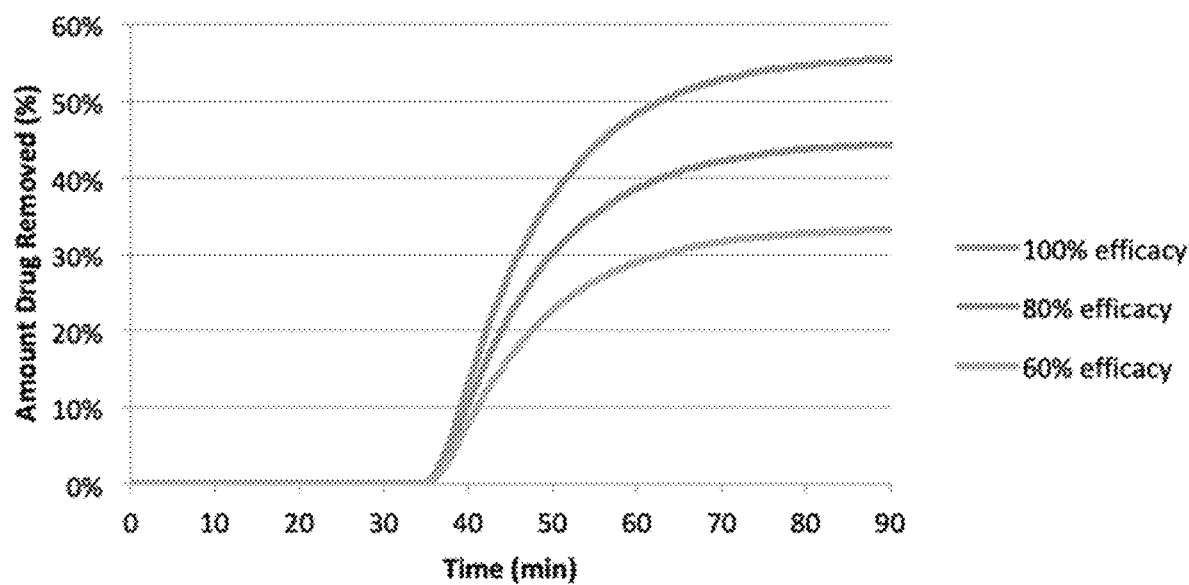
FIG. 13 is a graph of the total amount of drug removed (% of administered dose) for different filter efficacies based on a PK model of a human patients according to one embodiment. 56% of the injected dose could be removed with an ideal filter, ~44% could be removed with a filter of 80% efficacy, and 32% could be removed with a filter of 60% efficacy.

Human PK Model:

Physiologic parameters of humans were used from the literature. We assumed administration of TSL-Dox at a dose of 40 mg/m$^2$, which is a bit below the maximum tolerated dose of 50 mg/m$^2$ [6]. Clearance of encapsulated drug was considered based on published data in human patients, with a TSL-Dox formulation currently in clinical trials [6]. We assumed a filter flow rate of 350 mL/min, which is the maximum flow rate for a commercially available activated carbon filter for clinical use in humans [7]. We assumed a filtration rate of 80% based on studies in human patients where an activated carbon filter was used to remove doxorubicin during isolated liver perfusion [8]. FIG. 12 shows the plasma concentration of encapsulated drug with, and without filter. FIG. 13 shows the total amount of drug removed based on filter efficacy, suggesting that up to 56% of the injected dose could be removed under ideal conditions, and ~44% could be removed with a filter of 80% efficacy.

With reference now to FIG. 12, the plasma concentration of encapsulated drugs in the pharmacokinetic (PK) model based on the TSL-Dox formulation currently in human trials is shown. Encapsulated drug (thermosensitive liposomal doxorubicin (TSL-Dox)) was administered during the first 5 min, and filtration was started 30 min after drug administration.

Figure 4:
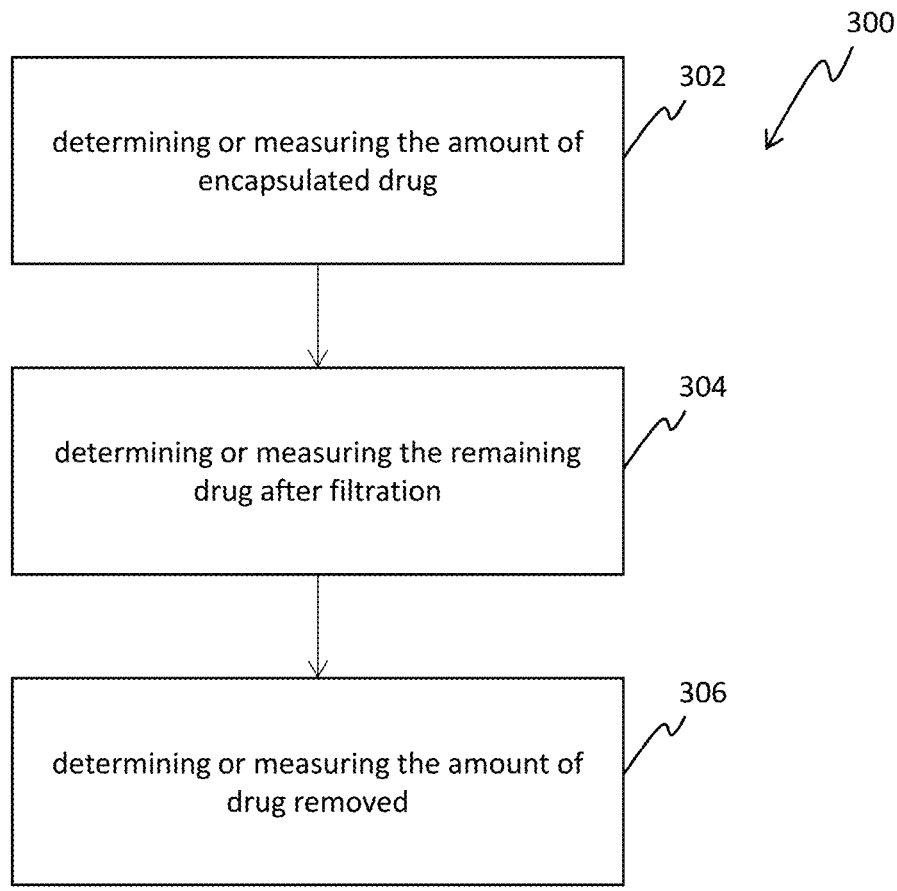
FIG. 4 is a flow chart of a method for reducing toxicity from intravascular triggered drug delivery according to one embodiment.

With reference now to FIG. 4, the total amount of drug removed (% of administered dose) for different filter efficacies based on a PK model of a human patients is shown. 56% of the injected dose could be removed with an ideal filter, ~44% could be removed with a filter of 80% efficacy, and 32% could be removed with a filter of 60% efficacy.

Experimental Example 4

In Vitro Studies with a Second Compound

To demonstrate that the proposed approach is more widely applicable, we performed in vitro studies with a second fluorescent chemotherapy agent, idarubicin. This agent is currently only used for blood cancer treatment in human patients, but may be effective for solid tumors as well if targeted delivery is used based on recent preclinical studies.

Figure 14:
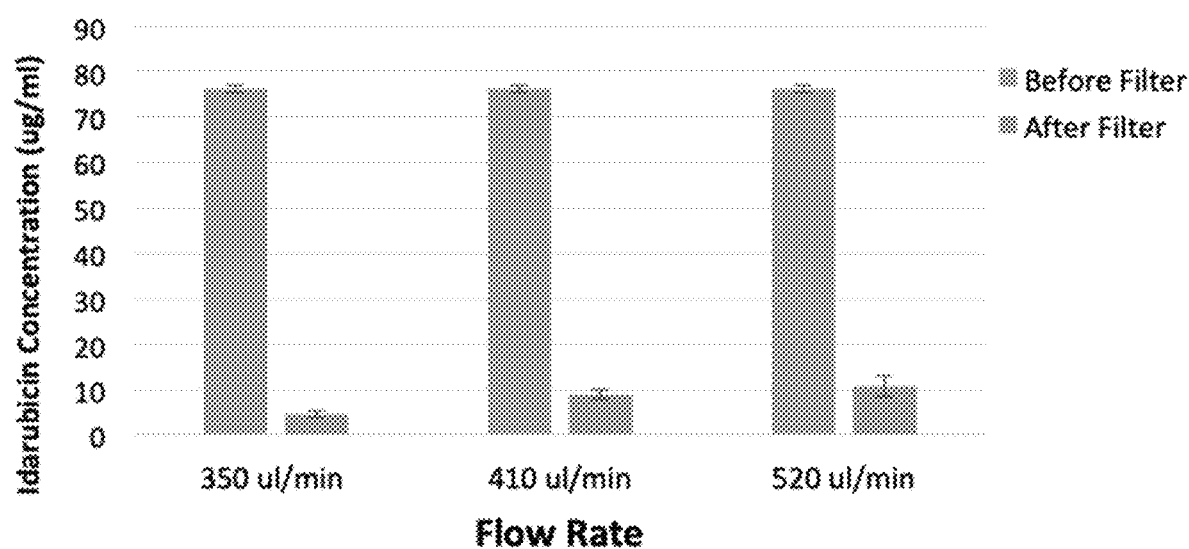
FIG. 14 is a graph of unencapsulated idarubicin dissolved in PBS (75 mg/ml), and pumped at flow rates of 350, 410 and 520 ul/min (n=3 for each case) through an activated carbon filter (filled with 175 mg of carbon pellets) according to one embodiment. Filtration efficacy was 95% at 350 ul/min, and 85% at 520 ul/min. For comparison, filter efficacy for doxorubicin was 90% at 350 ul/min with this filter.

First, we performed a study to demonstrate the ability to remove indarubicin in unencapsulated form with the activated carbon filter we used in our prior studies with doxorubicin. Idarubicin was dissolved in phosphate buffered saline (PBS) at a concentration of 75 ug/ml, and the solution was pumped through the same activated carbon filter that has been used in our past studies. FIG. 14 shows the drug concentration before and after the filter, demonstrating a filter efficacy of 85-95% at the examined flow rates. Unencapsulated idarubicin was dissolved in PBS (75 mg/ml), and pumped at flow rates of 350, 410 and 520 ul/min (n=3 for each case) through an activated carbon filter (filled with 175 mg of carbon pellets). Filtration efficacy was 95% at 350 ul/min, and 85% at 520 ul/min. For comparison, filter efficacy for doxorubicin was 90% at 350 ul/min with this filter.

Figure 15:
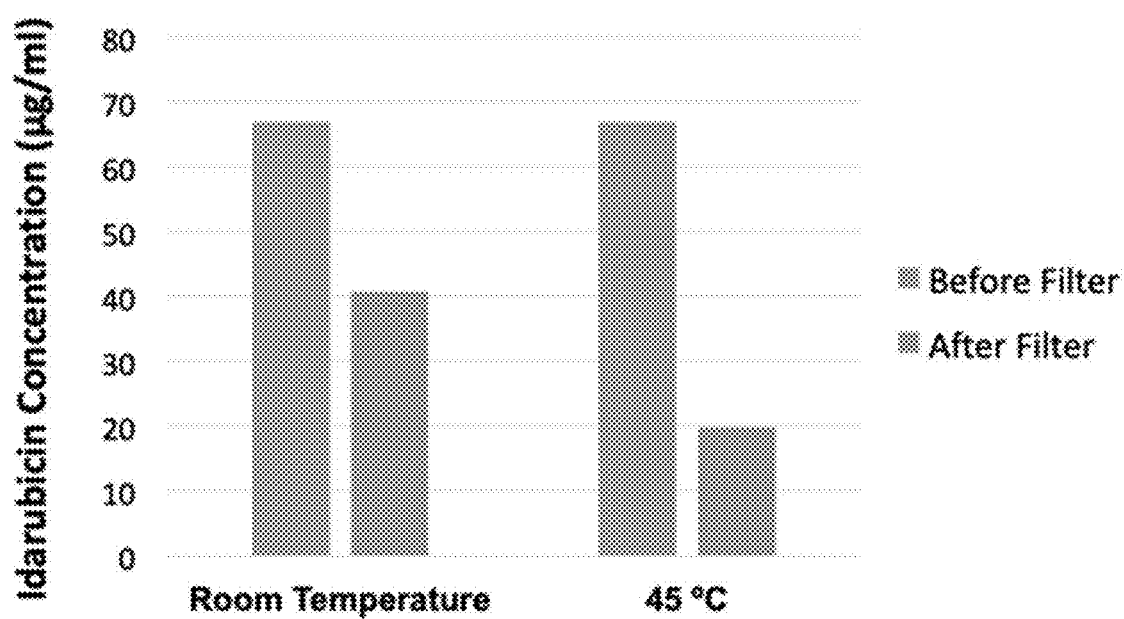
FIG. 15 is a graph of idarubicin encapsulated in thermosensitive liposomes (TSL) was dissolved in PBS (75 mg/ml) according to one embodiment. The solution was first exposed either to room temperature or to 45° C., and then pumped at a flowrate of 350 uL/min through the activated carbon filter. The graph shows the drug concentration before, and after the filter. At room temperature about 40% of the drug was removed by the filter (suggesting considerable leakage of idarubicin from TSL without heat exposure), and ~70% of the drug was removed after pre-heating to 45° C.

In a second study, idarubicin was encapsulated in thermosensitive liposomes (TSL). These TSL were of the same composition as we used for doxorubicin, i.e. the TSL were not optimized for the new compound and release kinetics are thus not ideal based on the results below. A solution of idarubicin encapsulated in TSL was dissolved in PBS, and was first exposed either to room temperature or to 45° C., followed by being pumped through the activated carbon filter. FIG. 15 shows that ~70% of the drug was removed by the filter when the solution was heated to 45° C., and 40% was removed when TSL were exposed to room temperature. Idarubicin encapsulated in thermosensitive liposomes (TSL) was dissolved in PBS (75 mg/ml). The solution was first exposed either to room temperature or to 45° C., and then pumped at a flowrate of 350 uL/min through the activated carbon filter. The graph shows the drug concentration before, and after the filter. At room temperature about 40% of the drug was removed by the filter (suggesting considerable leakage of idarubicin from TSL without heat exposure), and ~70% of the drug was removed after pre-heating to 45° C. These results suggest both considerable leakage of idarubicin from TSL at room temperature, as well as incomplete release after heating due to the TSL formulation not yet optimized. Nevertheless, this study demonstrates that the proposed approach is applicable to other drugs than doxorubicin.

Fluorescence monitoring to quantify drug concentration can be used, and for that purpose any naturally fluorescent drugs (e.g. topotecan, methotrexate, doxorubicin, idarubicin, epirubicin, pirarubicin) or fluorescently labeled drugs (e.g. cisplatin, carboplatin) may be used.

Idarubicin encapsulated in thermosensitive liposomes (TSL) was dissolved in PBS (75 mg/ml). The solution was first exposed either to room temperature or to 45° C., and then pumped at a flowrate of 350 uL/min through the activated carbon filter. The graph shows the drug concentration before, and after the filter. At room temperature about 40% of the drug was removed by the filter (suggesting considerable leakage of idarubicin from TSL without heat exposure), and ~70% of the drug was removed after pre-heating to 45° C.

REFERENCES CITED

[1] A. A. Manzoor, L. H. Lindner, C. D. Landon, J.-Y. Park, A. J. Simnick, M. R. Dreher, et al., "Overcoming Limitations in Nanoparticle Drug Delivery: Triggered, Intravascular Release to Improve Drug Penetration into Tumors," *Cancer Research*, vol. 72, pp. 5566-75, Sep. 4, 2012 2012.

[2] A. Gasselhuber, M. R. Dreher, F. Rattay, B. J. Wood, and D. Haemmerich, "Comparison of conventional chemotherapy, stealth liposomes and temperature-sensitive liposomes in a mathematical model," *PLoS One*, vol. 7, p. e47453, 2012.

[3] J. Eckes, O. Schmah, J. W. Siebers, U. Groh, S. Zschiedrich, B. Rautenberg, et al., "Kinetic targeting of pegylated liposomal doxorubicin: a new approach to reduce toxicity during chemotherapy (CARL-trial)," *BMC Cancer*, vol. 11, p. 337, 2011.

[4] D. A. August, N. Verma, M. A. Vaertan, R. Shah, and D. E. Brenner, "An evaluation of hepatic extraction and clearance of doxorubicin," *Br J Cancer*, vol. 72, pp. 65-71, July 1995.

[5] Mura S, Nicolas J, Couvreur P, Stimuli-responsive nanocarriers for drug delivery, Nat Mater 2013.

[6] Wood B J et al, Phase I Study of Heat-Deployed Liposomal Doxorubicin during Radiofrequency Ablation for Hepatic Malignancies, *J Vasc Interv Radiol* 23:248-55, 2012.

[7] Gambro, PrismafleX eXeed, Adsorba 300C activated charcoal cartridge.

[8] Ravikumar T S et al, Percutaneous hepatic vein isolation and high-dose hepatic arterial infusion chemotherapy for unresectable liver tumors, *J Clin Onc* 12: 2723-36, 1994.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A method for reducing toxicity from intravascular triggered drug delivery comprising:
    removing blood comprising an intravascular triggered drug delivery system from a patient's vascular system and delivering the blood to a chamber;
    applying a trigger to the blood to release a drug from the intravascular triggered drug delivery system;
    filtering the drug from the blood; and
    returning the filtered blood to the patient.
2. The method of claim 1; wherein trigger comprises the application of heat.
3. The method of claim 1, wherein trigger comprises the application of ultrasound.
4. The method of claim 1, wherein trigger comprises the application of a laser.
5. The method of claim 1, wherein trigger comprises the application of light.
6. The method of claim 1, wherein trigger comprises the application of a biological signal.
7. The method of claim 1 further comprising:
    plasma filtration, fluorescence or light absorption sensing performed on plasma.

* * * * *